United States Patent
Ebube et al.

(10) Patent No.: US 6,906,045 B2
(45) Date of Patent: Jun. 14, 2005

(54) METHOD FOR REDUCING MALODOR OF CHONDROITIN

(75) Inventors: Nkere Kanu Ebube, Glen Allen, VA (US); William Antonio Mark, Mechanicsville, VA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/094,096

(22) Filed: Mar. 8, 2002

(65) Prior Publication Data

US 2002/0141963 A1 Oct. 3, 2002

Related U.S. Application Data

(60) Provisional application No. 60/274,806, filed on Mar. 9, 2001.

(51) Int. Cl.[7] .................. A61K 31/737; C08B 37/08; A61L 9/00

(52) U.S. Cl. ................. 514/54; 536/55.1; 536/55.2; 536/123; 536/123.1; 424/76.1

(58) Field of Search .................. 424/76.1, 725; 514/54, 840; 536/55.1, 1.11, 55.2, 123

(56) References Cited

U.S. PATENT DOCUMENTS 6,358,539 B1 * 3/2002 Murad ................. 424/725

* cited by examiner

*Primary Examiner*—James O. Wilson
*Assistant Examiner*—Ganapathy Krishnan
(74) *Attorney, Agent, or Firm*—Steven H. Flynn

(57) ABSTRACT

The present invention relates to a method of removing or masking odor associated with chondroitin derived from marine life. The method comprises blending the chondroitin with citric acid, silicon dioxide, and optionally a flavorant to yield a substantially non-malodorous blend.

14 Claims, No Drawings

METHOD FOR REDUCING MALODOR OF CHONDROITIN

This application claims priority from copending provisional application Ser. No. 60/274,806, filed Mar. 9, 2001, the entire disclosure of which is hereby incorporated by reference.

FIELD OF THE INVENTION

The present invention relates to a method for the removal or masking of malodor from chondroitin derived from marine life. The present invention also relates to chondroitin compositions derived from marine life which lack a malodor.

BACKGROUND OF THE INVENTION

Chondroitin and glucosamine are chondroprotective agents used for the treatment of osteoarthritis and related diseases. Chondroitin sulfate is a soluble mucopolysaccharide derived from bovine, ovine or shark cartilage. Chondroitin sulfate derived from marine life, such as cartilage isolated from sharks, provides a rich, pure, and readily absorbed source of chondroitin.

Chondroitin sulfate has been reported to be effective in tissue repair and cartilage regeneration. Combinations of glucosamine and chondroitin are also effective in cartilage regeneration and joint maintenance. Chondroitin and glucosamine appear to act by increasing chondrocyte anabolic activity and suppressing degradative action of mediators on cartilage. This appears to facilitate natural tissue repair. See, e.g., H. Benedikt, *Nat. Pharm.*, 1(8): 1, 22 (1997) and C. Bassleer, et al., *Int. J. Tiss. Reac.* XIV(5): 231–241: (1992). Additionally, chondroitin and glucosamine are believed to be safer and less toxic than steroids or non-steroidal anti-inflammatory drugs commonly administered to treat arthritis and related musculo-skeletal diseases.

Although shark cartilage is rich source of chondroitin, shark-derived chondroitin has a strong malodor.

Therefore, there is a need for compositions containing shark-derived chondroitin without its malodor and methods of preparing the same. Removal of the malodor associated with such chondroitin would improve consumer acceptability and enhance patient compliance.

OBJECT OF THE INVENTION

It is an object of the invention to provide a method for removing and/or reducing the malodor associated with chondroitin derived from marine life. It is further an object of the invention to provide chondroitin derived from marine life which exhibits reduced levels of malodor normally associated with such a composition.

SUMMARY OF THE INVENTION

The invention relates to a method of removing or masking odor associated with chondroitin sulfate. The method comprises blending the chondroitin with citric acid, silicon dioxide, and, optionally a flavorant, to yield a substantially nonmalodorous blend. The blend may be formed into a solid dosage form, such as a tablet.

Another embodiment of the invention is a composition comprising chondroitin, citric acid, silicon dioxide, and an optional flavorant.

DETAILED DESCRIPTION OF THE INVENTION

The present inventors have discovered that the malodor associated with chondroitin derived from marine life may be removed or masked by blending the chondroitin with citric acid and silicon dioxide. Chondroitin compositions produced through the use of the present invention exhibit reduced levels of the malodor normally associated with such chondroitin compositions derived from marine sources.

The chondroitin may be any chondroitin-containing composition. Commonly available are two salts, namely chondroitin sulfate or chondroitin hydrochloride. Preferably, the chondroitin is the sulfate salt and is derived from shark cartilage. Most preferably, the chondroitin is water soluble, such as Polychon 60/40 available from Vanson, Inc. (Pfanstiehl Laboratory Inc.) of Waukegan, Ill.

The amount of citric acid in the composition broadly ranges from about 0.05 to about 10% percent by weight based upon 100 percent by weight of total composition. Preferably, the amount of citric acid in the composition is about 1.5 percent by weight on the same basis.

The amount of silicon dioxide in the composition ranges broadly from about 0.01 to about 2.0 percent by weight based upon 100 percent by weight of total composition. Preferably, the amount of silicon dioxide in the composition is preferably about 0.2 percent by weight on the same basis.

Other adjuvants as known to those in the art, such as disintegrants, antioxidants, lubricants and binders, may be included in the composition.

Optionally, the composition may contain a flavorant. The flavorant may be a natural flavorant, an artificial flavorant, or a combination thereof. Preferred flavorants include, but are not limited to, natural lemon extract, artificial lemon extract, natural orange extract, and any combination of any of the foregoing. The composition may contain an amount of flavorant effective in masking any degree of malodor remaining in the chondroitin-containing composition. The amount of flavorant in the composition broadly ranges from 0.0 to about 10 percent by weight based upon 100 percent by weight of total composition. Preferably, the flavorant is present in the composition in an amount of about 3.3 percent by weight on the same basis.

Combinations of chondroitin and glucosamine compounds are popular. Therefore, glucosamine or a salt thereof, may also be included in the composition. Preferred salts of glucosamine include, but are not limited to, glucosamine hydrochloride and glucosamine sulfate. The weight ratio of chondroitin sulfate to glucosamine generally ranges from about 1:100 to about 100:1. The typical mixture found in the composition which are currently commercialized have a weight ratio of about 5:4. Therefore, the preferred weight ratio of glucosamine to chondroitin is about 5:4. A preferred glucosamine is glucosamine hydrochloride, such as that produced by Wilke International of 15036 W. 106$^{th}$ Street, Lexexa, Kans. 66215.

The composition may be incorporated into or formed into solid dosage forms, such as capsules or tablets.

The claimed composition may be prepared by blending the chondroitin compound with citric acid, silicon dioxide, and optionally a flavorant. Preferably, citric acid, silicon dioxide, and the flavorant are mixed to form a citric acid/silicon dioxide/flavorant mixture prior to blending with the chondroitin sulfate. The citric acid/silicon dioxide/flavorant mixture is preferably prepared by mixing silicon dioxide and the flavorant and then adding citric acid.

EXAMPLE

The following example illustrates the invention without limitations. All amounts are by weight unless otherwise specified.

Example 1

Silicon dioxide (3.0 mg) available as Aerosil from Degussa-Huls Corporation of Ridgefield Park, N.J. was blended with 49.5 mg of natural lemon extract for about 3 minutes in a PK blender (manufactured by Patterson & Keely, a divson of Harsco Corporation, East Stroudsburg, Pa. 18301). Citric acid (22.5 mg) was added to the silicon dioxide/lemon extract blend and blended for about 2 minutes.

A 5:4 mixture of glucosamine sulfate and chondroitin sulfate was prepared by mixing in a mixing bowl with a PK Blender 750 grams of glucosamine hydrochloride (marketed by Pfanstiehl Laboratory Inc. of 1219 Glen Rock Avenue, Waukegan, Ill. 60085) and 600 grams of chondroitin sulfate (marketed under the tradename Polychon® 60/40 by Vanson, Inc. of Waukegan, Ill.). The mixture was placed into the feed hopper of a Fitzpatric IR-520 Chilsonator. The chilsonator converted the mixture into a compacted solid. The chilsonator was operated at a roll speed of 6 rpm, roll pressure of 1250 psig, vertical screw speed of 150 rpm, and horizontal screw speed of 15 rpm. The compacted product formed in the chilsonator was passed through a Fitzpatric M5A mill and the granulated product collected. The mill was operated at a rotor speed of 300 rpm with a 4 bar rotor and a 0.050 inch rasping screen. The relative humidity was 57% and the temperature was 75° F.

The chondroitin sulfate/glucosamine hydrochloride mixture, 30.0 mg of sodium starch glycolate, and 15.0 mg of magnesium stearate were added to the silicon dioxide/lemon extract/citric acid blend and blended for about 3 minutes. The resulting powder blend was then compressed into a tablet at a suitable compression pressure using a rotary tablet press and standard tooling. The resulting tablet did not exhibit any malodor, differing substantially from that exhibited by the initial chondroitin sulfate component.

Many variations of the present invention will suggest themselves to those skilled in the art in light of the above, detailed description. All such obvious variations are within the full intended scope of the appended claims.

What is claimed is:

1. A method of removing or masking odor associated with chondroitin derived from marine life, said method comprising blending said chondroitin with citric acid and silicon dioxide to yield a substantially non-malodorous blend.

2. The method as defined in claim 1, wherein said chondroitin is chondroitin sulfate.

3. The method as defined in claim 1, wherein said chondroitin is chondroitin sulfate derived from shark cartilage.

4. The method as defined in claim 1, wherein the amount of citric acid in said blend ranges from about 0.5 to about 10 percent by weight based upon 100 percent by weight of total blend.

5. The method as defined in claim 4, wherein the amount of citric acid in said blend is about 1.5 percent by weight, based upon 100 percent by weight of total blend.

6. The method as defined in claim 1, wherein the amount of said silicon dioxide in said blend ranges from about 0.01 to about 2.0 percent by weight, based upon 100 percent by weight of total blend.

7. The method as defined in claim 6, wherein the amount of said silicon dioxide in said blend is about 0.2 percent by weight, based upon 100 percent by weight of total blend.

8. The method of claim 1 wherein the blend contains a flavorant.

9. The method as defined in claim 8, wherein said flavorant is selected from the group consisting of natural flavorants, artificial flavorants, or a combination thereof.

10. The method of claim 8 wherein the flavorant is present in amount up to about 10 percent by weight, based upon 100 percent by weight of the total blend.

11. The method of claim 8 wherein the flavorant is present in an amount of about 3.3 percent by weight, based upon 100 percent by weight of the total blend.

12. The method of claim 1, wherein said blend further includes glucosamine or a salt thereof.

13. A method as defined in claim 12, wherein the weight ratio of glucosamine or salt thereof to chondroitin sulfate is about 5:4.

14. The method of claim 1, wherein said citric acid and silicon dioxide are preblended prior to contacting said chondroitin.

* * * * *